(12) United States Patent
Ishihara et al.

(10) Patent No.: US 12,127,606 B2
(45) Date of Patent: Oct. 29, 2024

(54) PANT-TYPE WEARABLE ARTICLE

(71) Applicant: The Procter & Gamble Company, Cincinnati, OH (US)

(72) Inventors: Kaoru Ishihara, West Chester, OH (US); Shiqiao Li, Beijing (CN); Xuechun Wang, Beijing (CN); Koichi Morimoto, Beijing (CN); John Andrew Strasemeier, Aurora, IN (US); Vanessa Marie Melendez, Cincinnati, OH (US); Monica Renee Tournoux, Columbus, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1073 days.

(21) Appl. No.: 16/787,437

(22) Filed: Feb. 11, 2020

(65) Prior Publication Data
US 2020/0260799 A1 Aug. 20, 2020

(51) Int. Cl.
*A61F 13/496* (2006.01)
*A41B 9/00* (2006.01)
(Continued)

(52) U.S. Cl.
CPC ........ *A41B 9/001* (2013.01); *A61F 13/49011* (2013.01); *A61F 13/49014* (2013.01);
(Continued)

(58) Field of Classification Search
CPC .......... A61F 13/49011; A61F 13/49014; A61F 13/49019; A61F 13/4963; A61F 13/5146
See application file for complete search history.

(56) References Cited

U.S. PATENT DOCUMENTS 5,628,097 A 5/1997 Benson et al.
7,582,348 B2 9/2009 Ando
(Continued)

FOREIGN PATENT DOCUMENTS

CN 1128494 A 8/1996
CN 1183714 A 6/1998
(Continued)

OTHER PUBLICATIONS

PCT International Search Report dated Apr. 17, 2020, 13 pages.
(Continued)

*Primary Examiner* — Jessica Arble
(74) *Attorney, Agent, or Firm* — Charles R. Matson

(57) ABSTRACT

Disclosed is a wearable article comprising front and back elastic belt regions and a crotch region between the front and back elastic belt regions; the front and back elastic belt regions each comprising a laminate, an elastic bonding continuously bonding an elastic member in the direction of stretch, and a vertical bonding applied to at least one of inner and outer sheets to intermittently bond the elastic member to at least one of the inner and outer sheets, the vertical bonding having a transverse dimension VG2 and spaced apart from each other with a transverse pitch VG1, wherein the outer sheet comprises a repeating pattern of apertures, the repeating pattern of apertures spaced apart from each other with a longitudinal pitch DF2, and spaced apart from each other with a transverse pitch DF1, wherein VG1 is greater than DF1, and wherein the repeating pattern of apertures have a Longitudinal Orientation.

6 Claims, 8 Drawing Sheets

FIG. 3B

(51) Int. Cl.
*A61F 13/49* (2006.01)
*A61F 13/514* (2006.01)

(52) U.S. Cl.
CPC .... *A61F 13/49019* (2013.01); *A61F 13/4963* (2013.01); *A61F 13/5146* (2013.01)

(56) References Cited

U.S. PATENT DOCUMENTS

| | | |
|---|---|---|
| 7,896,858 B2 | 3/2011 | Trennepohl |
| 8,395,017 B2 | 3/2013 | Nakahata |
| 9,339,421 B2 | 5/2016 | Glahn |
| 9,498,389 B2 | 11/2016 | Trennepohl |
| 9,517,168 B2 | 12/2016 | Trennepohl |
| 10,166,155 B2 | 1/2019 | Glahn |
| 10,307,302 B2 | 6/2019 | Trennepohl |
| 11,103,389 B2 * | 8/2021 | Takahashi ............ B29C 66/7294 |
| 2002/0049269 A1 | 4/2002 | Ho et al. |
| 2002/0173765 A1 | 11/2002 | Pargass et al. |
| 2004/0147890 A1 | 7/2004 | Nakahata |
| 2006/0047260 A1 | 3/2006 | Ashton |
| 2006/0149209 A1 | 7/2006 | Malchow et al. |
| 2006/0270302 A1 | 11/2006 | Ando |
| 2006/0282054 A1 | 12/2006 | Shimoe et al. |
| 2008/0000003 A1 | 1/2008 | Melander |
| 2010/0076394 A1 | 3/2010 | Hayase |
| 2011/0060304 A1 | 3/2011 | Otsubo |
| 2011/0112499 A1 | 5/2011 | Trennepohl |
| 2011/0203102 A1 | 8/2011 | Trennepohl |
| 2011/0203727 A1 | 8/2011 | Trennepohl |
| 2011/0203728 A1 | 8/2011 | Trennepohl |
| 2011/0208152 A1 | 8/2011 | Trennepohl |
| 2012/0095429 A1 | 4/2012 | Kobayashi |
| 2013/0253461 A1 | 9/2013 | Xu et al. |
| 2013/0310798 A1 | 11/2013 | Glahn |
| 2013/0317471 A1 | 11/2013 | Morimoto |
| 2015/0282999 A1 | 10/2015 | Arizti |
| 2016/0058627 A1 | 3/2016 | Barnes |
| 2017/0027770 A1 | 2/2017 | Glahn |
| 2017/0189244 A1 | 7/2017 | Mueller |
| 2017/0231837 A1 * | 8/2017 | Tashiro ............... A61F 13/5633 604/385.3 |
| 2017/0252229 A1 | 9/2017 | Bonelli |
| 2017/0281421 A1 | 10/2017 | Umemoto |
| 2017/0290711 A1 | 10/2017 | Morimoto |
| 2018/0008488 A1 | 1/2018 | Sheldon et al. |
| 2018/0168874 A1 | 6/2018 | Lavon |
| 2018/0168885 A1 | 6/2018 | Zink, II |
| 2018/0193207 A1 | 7/2018 | Hasegawa |
| 2018/0289563 A1 | 10/2018 | Morimoto |
| 2019/0021916 A1 | 1/2019 | Ishikawa |
| 2019/0060142 A1 | 2/2019 | Okuda |
| 2019/0076306 A1 | 3/2019 | Glahn |
| 2019/0201253 A1 | 7/2019 | Fukae |
| 2019/0247245 A1 | 8/2019 | Morimoto et al. |
| 2019/0254882 A1 | 8/2019 | Trennepohl |
| 2019/0314216 A1 | 10/2019 | Bäck |
| 2019/0358093 A1 | 11/2019 | Kaufman et al. |
| 2019/0388282 A1 | 12/2019 | Enz et al. |
| 2020/0206042 A1 | 7/2020 | Morimoto et al. |
| 2020/0260798 A1 | 8/2020 | Morimoto et al. |
| 2020/0261282 A1 | 8/2020 | Li et al. |
| 2020/0297552 A1 | 9/2020 | Ono et al. |
| 2020/0315866 A1 | 10/2020 | Fukae et al. |
| 2020/0397622 A1 * | 12/2020 | Ono ..................... A61F 13/496 |
| 2021/0069031 A1 | 3/2021 | Shimizu et al. |

FOREIGN PATENT DOCUMENTS

| | | |
|---|---|---|
| CN | 1646074 A | 7/2005 |
| CN | 1784191 A | 6/2006 |
| CN | 101123931 A | 2/2008 |
| CN | 101541284 B | 1/2013 |
| CN | 202908952 U | 5/2013 |
| CN | 104507433 A | 4/2015 |
| CN | 204428283 U | 7/2015 |
| CN | 204909840 U | 12/2015 |
| CN | 102871802 B | 6/2016 |
| CN | 106029028 A | 10/2016 |
| CN | 106456403 A | 2/2017 |
| CN | 106659603 A | 5/2017 |
| CN | 106794090 A | 5/2017 |
| CN | 107260401 A | 10/2017 |
| CN | 107260404 A | 10/2017 |
| CN | 107847373 A | 3/2018 |
| CN | 207785374 U | 8/2018 |
| CN | 108601686 A | 9/2018 |
| CN | 108601687 A | 9/2018 |
| CN | 104349761 B | 11/2018 |
| CN | 208160703 U | 11/2018 |
| CN | 109069323 A | 12/2018 |
| CN | 113382704 A | 9/2021 |
| EP | 1559386 A2 | 8/2005 |
| EP | 3117810 A1 | 1/2017 |
| EP | 3326595 A1 | 5/2018 |
| JP | 2004254862 | 9/2004 |
| JP | 2004298467 A | 10/2004 |
| JP | 2007068819 A | 3/2007 |
| JP | 2010246901 A | 11/2010 |
| JP | 2011078477 A | 4/2011 |
| JP | 5535569 B2 | 7/2014 |
| JP | 2015104608 A | 6/2015 |
| JP | 2015128573 A | 7/2015 |
| JP | 2016022235 A | 2/2016 |
| JP | 2016536176 A | 11/2016 |
| JP | 2017104197 A | 6/2017 |
| JP | 2022520380 A | 3/2022 |
| WO | WO2005025789 A1 | 3/2005 |
| WO | WO2006017718 A1 | 2/2006 |
| WO | WO2011087503 A1 | 7/2011 |
| WO | WO2011122604 A1 | 10/2011 |
| WO | 2015182441 A1 | 12/2015 |
| WO | WO2016073712 A1 | 5/2016 |
| WO | 2017163753 A1 | 9/2017 |
| WO | WO2018118581 A1 | 6/2018 |
| WO | 2018153106 A1 | 8/2018 |
| WO | 2018235211 A1 | 12/2018 |
| WO | WO2019026529 A1 | 2/2019 |
| WO | 2019169989 A1 | 9/2019 |

OTHER PUBLICATIONS

PCT International Search Report dated Apr. 17, 2020, 12 pages.
PCT Search Report and Written Opinion for PCT/CN2020/073546 dated Apr. 17, 2020, 10 pages.
All Office Actions; U.S. Appl. No. 16/787,207, filed on Feb. 11, 2020.
All Office Actions; U.S. Appl. No. 16/787,548, filed on Feb. 11, 2020.
PCT International Search Report dated Oct. 30, 2019, 11 pages.
PCT International Search Report dated Nov. 15, 2019, 12 pages.
PCT International Search Report dated Nov. 13, 2019, 12 pages.
PCT Suppl. Search Report and Written Opinion for PCT/CN2020/073546 dated May 26, 2021, 12 pages.

* cited by examiner

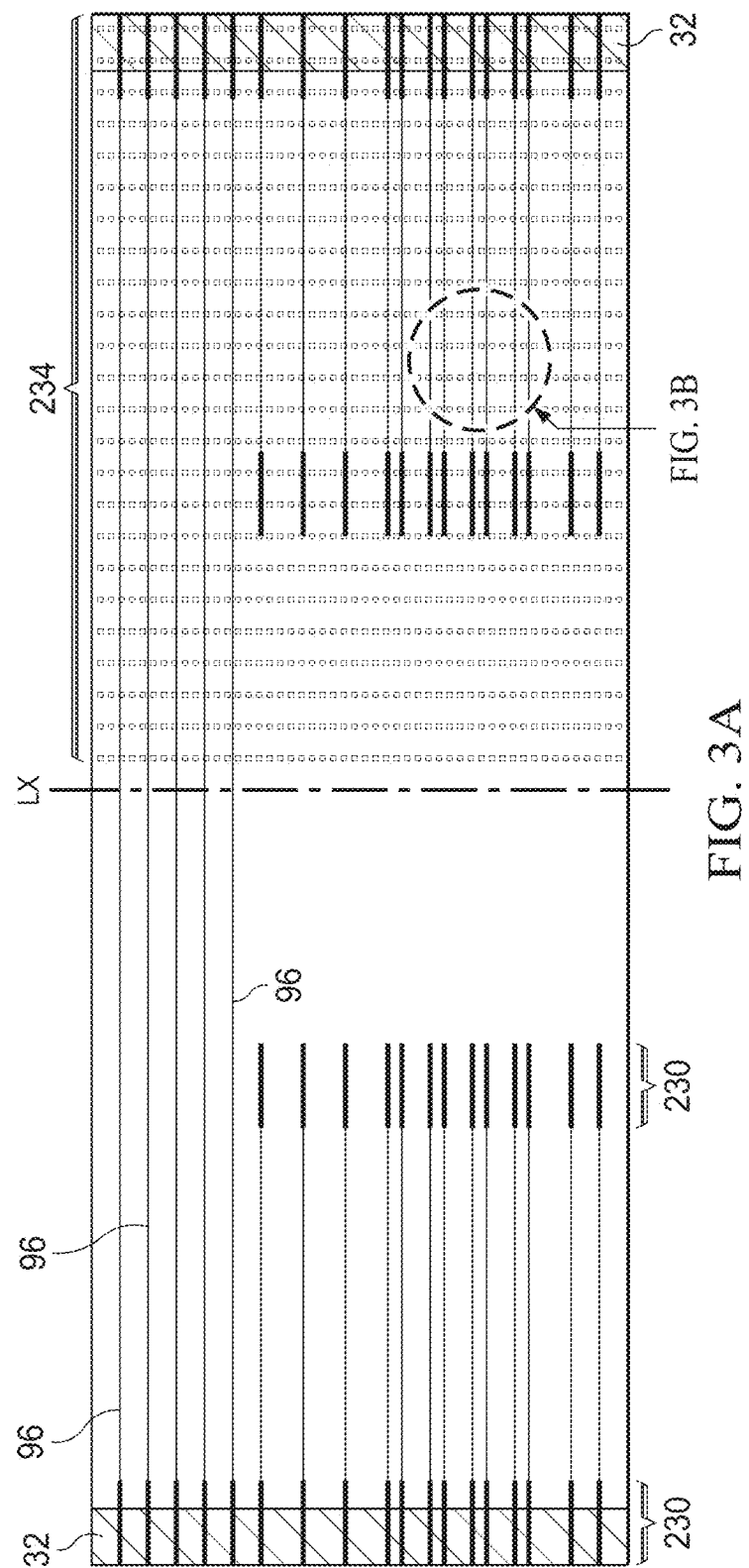

PANT-TYPE WEARABLE ARTICLE

CROSS REFERENCE TO RELATED APPLICATIONS

This application claims priority to Chinese PCT Patent Application No. PCT/CN2020/073546, filed on Jan. 21, 2020, and to Chinese PCT Patent Application No. PCT/CN2019/075101, filed on Feb. 14, 2019, both of which are incorporated by reference herein.

FIELD OF THE INVENTION

The present invention relates to pant-type wearable articles having an elastic belt with improved regularity of gathers and visibility of apertures.

BACKGROUND OF THE INVENTION

Infants and other incontinent individuals wear absorbent articles such as diapers to receive and contain urine and other body exudates. Pull-on absorbent articles, or pant-type absorbent articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tends to be more difficult, and also for younger babies requiring a soft fit around the waist opening and leg openings.

Pant-type articles may take various structures wherein the circumference of the waist opening and vicinity thereof is made elastic enough to facilitate the wearer or the caregiver to expand the article and insert the wearer's legs into the leg openings for wearing the article. The region of the waist circumference and vicinity thereof is often referred to as the elastic belt. One type of structure for the pant-type article is the belt-type pant having a central chassis to cover the crotch region of the wearer and a separate elastic belt defining the waist opening and leg opening, such as described in PCT Publication WO 2006/17718A. Another type of structure for the pant-type article is the uni-body pant configured such that the outer cover of the article completely covers the entirety of the garment-facing surface of the article, wherein the portion configured to stretch about the torso is considered the elastic belt region.

Whatever the structure of the pant-type article may be, pant-type articles provide only a very small range of size adjustment or body configuration adjustment based on the structural limitations of the article. As such, pant-type articles are typically so configured to accommodate size and configuration ranges by providing the elastic belt region very stretchable and comfortable to wear, yet with reliable fit such that sufficient protection against sagging and leakage may be provided. Further, the elastic belt region may be the portion which is most touched and observed by the wearer or the caregiver upon use, and thus its properties most associated with the quality of the article. By quality, what may be desired is an undergarment-like appearance provided by improved visibility and regularity of apertures. Having apertures on the article, and particularly the elastic belt region, may provide an intuitive signal to the wearer or caregiver of breathability and comfort. Further, regularity of apertures may further enhance high quality perception.

Based on the foregoing, there is a need for a wearable article providing improved stretchability for ease of application, improved fit for preventing sagging, improved comfort and softness, and improved breathability for skin health. There is also a need for a wearable article having improved regularity of gathers and visibility of apertures which intuitively communicates the functional benefits described above. There is also a need for providing such a wearable article which can be economically made.

SUMMARY OF THE INVENTION

The present invention is directed to a wearable article continuous in a longitudinal direction and a transverse direction comprising a front elastic belt region, a back elastic belt region, a crotch region, a waist opening, and a pair of leg openings; the crotch region extending longitudinally between the front elastic belt region and the back elastic belt region;

the front and back elastic belt regions each comprising a laminate, the laminate comprising an inner sheet, an outer sheet, an elastic member running in the transverse direction, an elastic bonding which continuously bonds the elastic member for at least about 10 mm in the direction of stretch in a region adjacent the side edges of the front and back elastic belts, and a vertical bonding applied to at least one of the inner sheet and the outer sheet with intervals in the transverse direction to intermittently bond the inner sheet and the outer sheet, the vertical bonding having a transverse dimension VG2 and spaced apart from each other with a transverse pitch VG1, wherein at least the outer sheet comprises a first repeating pattern of apertures wherein each aperture has an aspect ratio of no more than about 2 and a minor radius of at least about 0.1 mm, the first repeating pattern of apertures spaced apart from each other with a longitudinal pitch DF2 of no more than about 5 mm, and spaced apart from each other with a transverse pitch DF1, wherein VG1 is greater than DF1, preferably VG1 is at least about 1.5 times as DF1, and wherein the first repeating pattern of apertures have a Longitudinal Orientation, according to the measurements herein.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

FIG. 3A is a schematic plan view of the embodiment of FIG. 2 showing the elastic member positioning, elastic bondings and vertical bondings.

DEFINITIONS

Figure 1A:
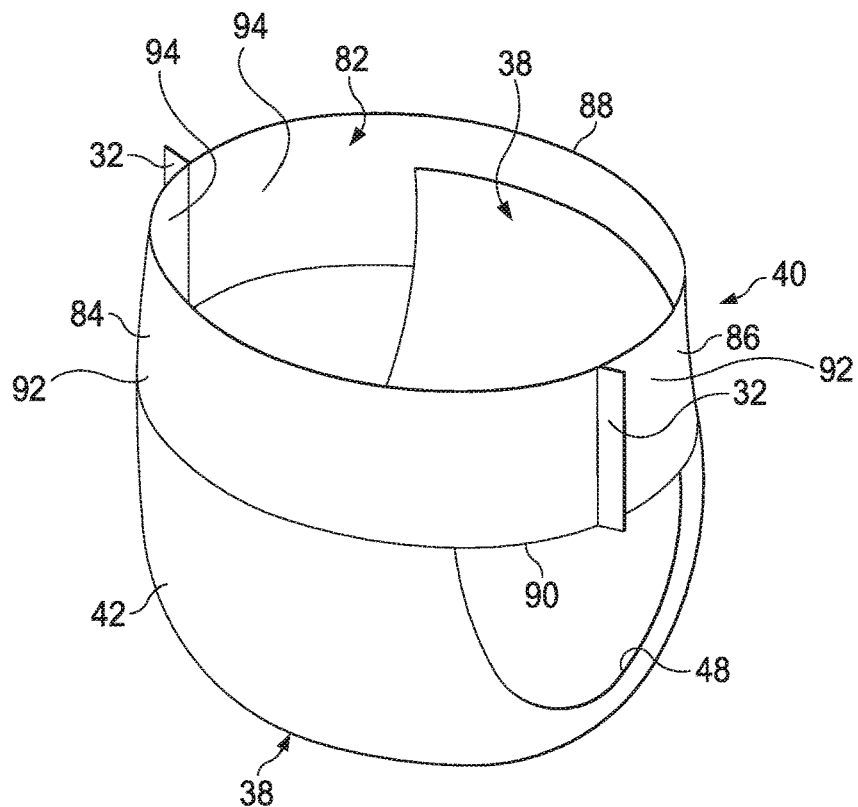
FIG. 1A is a perspective view of one embodiment of a wearable article of the present invention.

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Proximal" and "distal" refer respectively to the position closer or farther relative to the longitudinal center of the article.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Dimension", "Length", "Width", "Pitch", "Diameter", "Aspect Ratio", "Angle", and "Area" of the article are all measured in a state wherein the article is extended to the Full Stretch Circumference W1 according to the "Whole Article Force Measurement" herein, and utilizing a ruler or a loupe, unless specified otherwise.

"Artwork" refers to a visual presentation to the naked eye, which is provided by printing or otherwise, and having a color. Printing includes various methods and apparatus well known to those skilled in the art such as lithographic, screen printing, flexographic, and gravure ink jet printing techniques.

"Color" or "Colored" as referred to herein includes any primary color except color white, i.e., black, red, blue, violet, orange, yellow, green, and indigo as well as any declination thereof or mixture thereof. The color white is defined as those colors having a L* value of at least 94, an a* value equal to 0±2, and a b* value equal to 0±2 according to the CIE L* a* b* color system.

DETAILED DESCRIPTION OF THE INVENTION

Figure 1B:
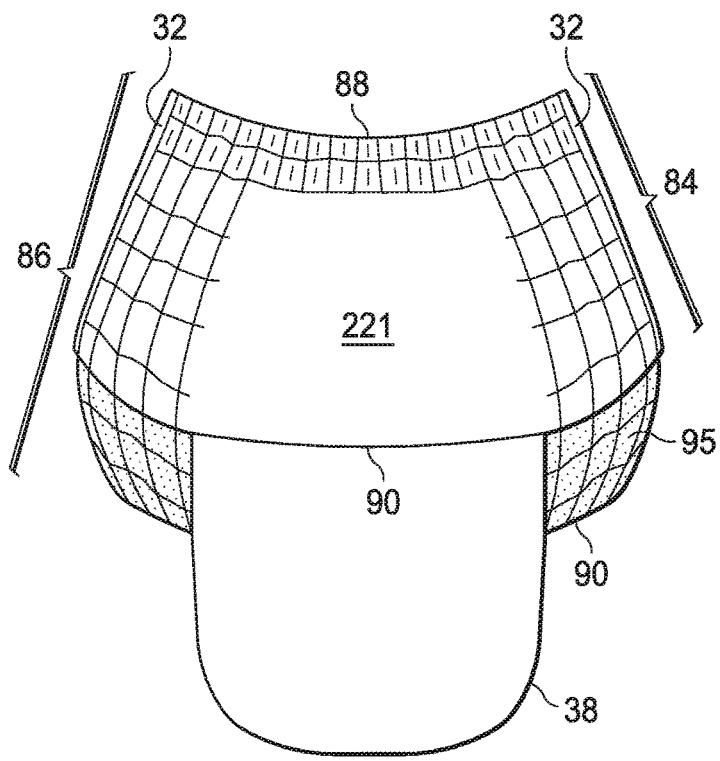
FIG. 1B is a schematic view of one embodiment of a wearable article of the present invention in a contracted state showing the front side of the article.
Figure 2:
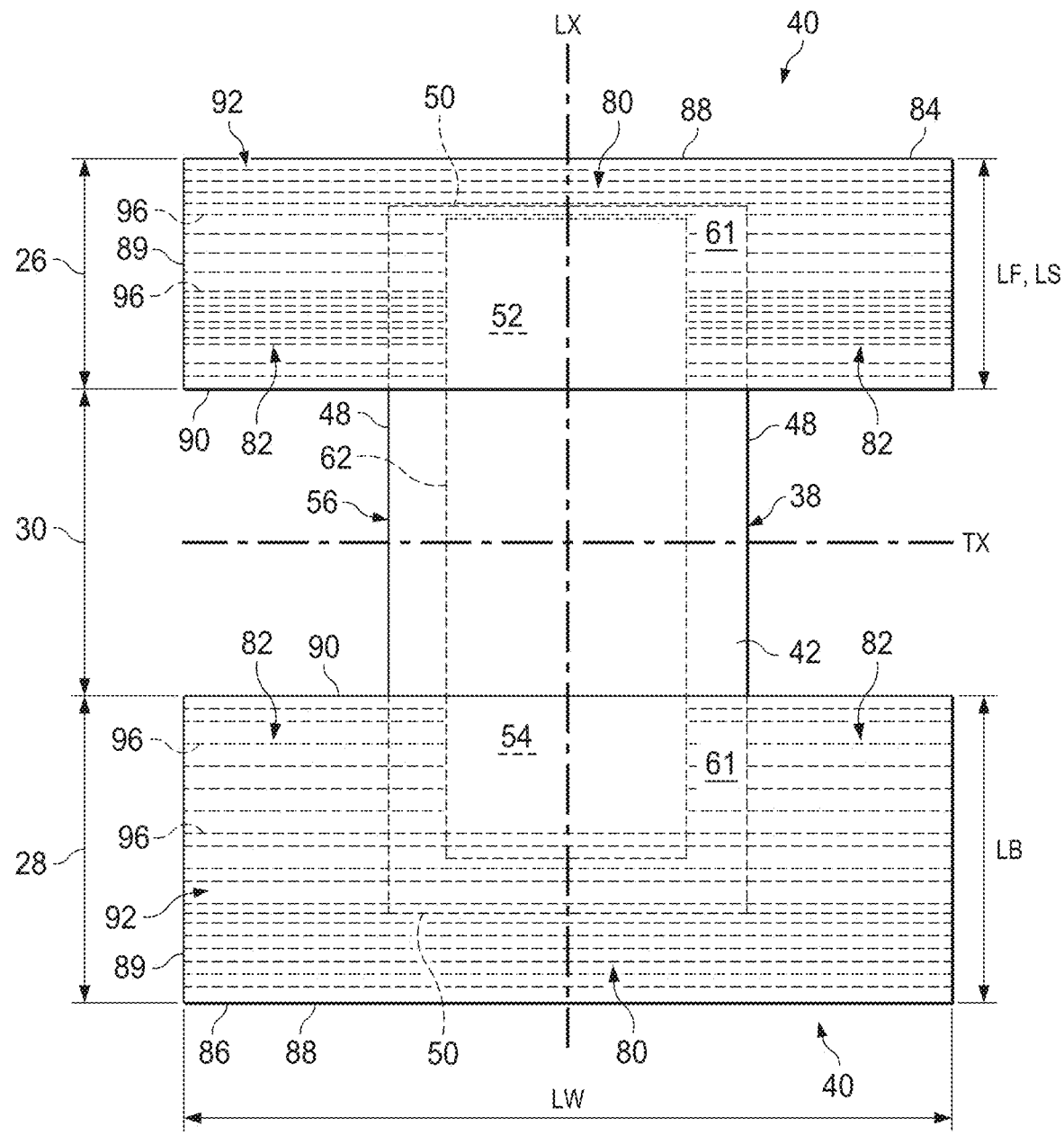
FIG. 2 is a schematic plan view of one embodiment of a wearable article of the present invention with the seams enjoined and in a flat uncontracted condition showing the garment facing surface.

FIG. 1A is a perspective view of a wearable article 20 of the present invention, FIG. 1B is a schematic view of a wearable article of the present invention in a contracted state showing the front side, and FIG. 2 is a schematic plan view of a wearable article with the seams unjoined and in its flat uncontracted condition showing the garment-facing surface. The wearable article 20 has a longitudinal centerline LX which also serves as the longitudinal axis, and a transverse centerline TX which also serves as the transverse axis. The wearable article 20 has a body facing surface, a garment facing surface, a front elastic belt 84, a back elastic belt 86, a crotch region 30, and side seams 32 which join the front elastic belt 84 and the back elastic belt 86, to form two leg openings and a waist opening.

The wearable article 20 may be a belt-type pant as in FIGS. 1A, 1B, and 2 comprising a central chassis 38 to cover the crotch region 30 of the wearer, a front elastic belt 84 and a back elastic belt 86 (hereinafter may be referred to as "front and back elastic belts"), the front and back elastic belts 84, 86 forming a discrete ring-like elastic belt 40 extending transversely defining the waist opening. For the belt-type pant, the discrete ring-like elastic belt 40 may also be referred to as the elastic belt 40. For the belt-type pant as in FIGS. 1A, 1B, and 2, the front and back elastic belts 84, 86 and the central chassis 38 jointly define the leg openings. For the belt-type pant, the front elastic belt 84 is the front region 26, and the back elastic belt 86 is the back region 28, and the remainder is the crotch region 30. While not shown, the wearable article 20 may be a uni-body type pant configured such that the outer cover of the central chassis 38 and the elastic belt 40 are common. For the uni-body type pant, the portion extending in the transverse direction between the side seams 32, respectively, are considered the front region 26 and the back region 28, and the remainder is the crotch region 30. For the uni-body type pant, the front region 26 is considered the front elastic belt 84, and the back region 28 is considered the back elastic belt 86.

The central chassis 38 may comprise a topsheet, a backsheet and an absorbent core 62 disposed between the topsheet and the backsheet, and further an outer cover layer 42 for covering the garment-facing side of the backsheet. The topsheet may be a water permeable substrate. The backsheet may be a water impermeable film. The outer cover layer 42 may be a nonwoven sheet. The central chassis 38 may contain an absorbent core 62 for absorbing and containing body exudates disposed on the central chassis 38, and an absorbent material non-existing region 61 surrounding the periphery of the absorbent core 62. The absorbent material non-existing region 61 may be made of the topsheet and/or the backsheet and/or the outer cover layer 42 and/or other parts configuring the central chassis 38. In the embodiment shown in FIG. 2, the central chassis 38 has a generally rectangular shape, left and right longitudinally extending side edges 48 and front and back transversely extending end edges 50. The absorbent core 62 may exist through the entire longitudinal dimension of the crotch region and extending at least partly in the front region 26; or at least partly in both the front and back regions 26, 28. The central chassis 38 may have a front waist panel 52 positioned in the front region 26 of the absorbent article 20, a back waist panel 54 positioned in the back region 28, and a crotch panel 56 between the front and back waist panels 52, 54 in the crotch region 30. The center of the front elastic belt 84 is joined to a front waist panel 52 of the central chassis 38, the center of the back elastic belt 86 is joined to a back waist panel 54 of the central chassis 38, the front and back elastic belts 84, 86 each having a left side panel and a right side panel 82 where the central chassis 38 does not overlap. The central chassis has a crotch panel 56 positioned between the front waist panel 52 and the back waist panel 54.

The absorbent core 62 may include an absorbent layer and an acquisition layer. The absorbent layer is the region wherein absorbent materials having a high retention capacity, such as superabsorbent polymers, are present. The absorbent layer may be substantially cellulose free. Superabsorbent polymers of the absorbent layer may be disposed between first and second layers of material immobilized by a fibrous layer of thermoplastic adhesive material. The first and second layers of materials may be nonwoven fibrous webs including synthetic fibers, such as mono-constituent fibers of PE, PET and PP, multiconstituent fibers such as side by side, core/sheath or island in the sea type fibers. Such synthetic fibers may be formed via a spunbonding process or a meltblowing process. The acquisition layer facilitates the acquisition and the distribution of body exudates and may be placed between the topsheet and the absorbent layer. The acquisition layer may include cellulosic fibers.

The absorbent layers may be disposed in plurality in the absorbent core 62. Some portions of the absorbent layers may be configured to have substantially no absorbent material to form a channel or a plurality of channels. Channels may be useful for allowing the absorbent core 62 to bend upon swelling with fluids, such that the absorbent article conforms to the wearer's body after swelling and prevent sagging of the article. The channels may also be formed in the acquisition layer, and may be configured to at least partly match the channels of the absorbent layer in the thickness direction.

The elastic belt 40 of the article of the present invention acts to dynamically create fitment forces and to distribute the forces dynamically generated during wear. The front and back elastic belts 84, 86 may be joined with each other only at the side edges 89 to form side seams 32, a waist opening and two leg openings. Each leg opening may be provided with elasticity around the perimeter of the leg opening. The elasticity around the leg opening may be provided by the combination of elasticity from the front belt 84, the back belt 86, and the central chassis 38.

The longitudinal length of the backsheet and the outer cover layer 42 may be the same, or may be varied. For example, the outer cover layer 42 may have a shorter length compared to that of the backsheet, such that the outer cover layer 42 is devoid where the central chassis 38 overlaps the elastic belt 40. By such configuration, the elastic belt may have better breathability. Further, such configuration may provide cost saving. The transverse width of the backsheet and the outer cover layer 42 may be the same, or may be varied. For example, the backsheet may have a shorter transverse width compared to that of the outer cover layer 42. By such configuration, the longitudinal side edges 48 of the crotch panel 56, which make part of the leg openings, may have better breathability. Further, such configuration may provide cost saving.

The front elastic belt 84 and back elastic belt 86 are configured to impart elasticity to the belt 40. Referring to FIGS. 1B and 2, the front belt 84 and the back belt 86 may each comprise a laminate, the laminate comprising a plurality of elastic members 96 running in the transverse direction, an inner sheet 94, an outer sheet 92, and an outer sheet fold over (not shown) wherein the outer sheet fold over is an extension of the outer sheet material formed by folding the outer sheet material at the distal edge 88 of the front and back belts; wherein the belt elastic members 96 are sandwiched between two of these sheets. The front elastic belt 84 and the back elastic belt 86 may each be made only by elastic members 96, the inner sheet 94, the outer sheet 92, and the outer sheet fold over. The belt elastic members 96 may extend in the transverse direction to provide a ring like elastic belt 40 when the front elastic belt 84 and the back elastic belt 86 are joined. At least some of the elastic members 96 extend in the transverse direction substantially parallel to each other. All of the elastic members 96 may extend in the transverse direction substantially parallel to each other. Such an article may be economically made. The front and back elastic belt 84, 86 each may have transversely continuous proximal and distal edges, the proximal edge 90 being located closer than the distal edge 88 relative to the longitudinal center of the article. At least 10%, or at least from about 15% to not more than about 70%, of the front and back elastic belts from the waist opening in the longitudinal direction may be a laminate in active elasticity along the entire transverse dimension LW of the front and back elastic belts 84, 86. These regions of the front and back elastic belts 84, 86 in active elasticity are defined as the Upper Gather Region 220. Referring to FIGS. 1B and 2, the front and back elastic belts 84, 86 may be treated such that certain regions are removed of its elastic activity to form a non-elastic region 221. For each front and back elastic belt 84, 86, the region overlapping the front and/or back waist panel 52, 54 of the central chassis 38 may be removed of its elastic activity and defining the non-elastic region 221.

The elastic belt region 40 may be closely associated with the function and quality of the article. Having apertures on the elastic belt 40 enhances breathability. When such apertures are visible from the garment facing side, this may provide an intuitive signal to the wearer or caregiver of breathability and comfort. Thus, at least the outer sheet may be provided with a first repeating pattern of apertures. Materials for forming the elastic belt region 40, as well as positioning of the apertures, and visibility of the apertures, are carefully planned by the manufacturer for providing the desirables for the article. An undergarment kind of appearance and aesthetically pleasing regularity of apertures may be associated with high quality. Pleasant tactile sense such as flexibility and cushiony touch may also enhance perception of high quality. Stretchability for ease of application, fit for preventing sagging, comfort and softness, may also be associated with high function. Highly aesthetically pleasing apertures and gathers which intuitively communicate the functional benefits described above provide the favorable entire usage experience of the article by the user. The user may be the wearer or the caregiver.

At least the outer sheet 92 comprises a first repeating pattern of apertures. The first repeating pattern of apertures may have a Longitudinal Orientation, according to the measurements herein. What is described by the Longitudinal Orientation is the longitudinally directed impression that the naked eye perceives when observing the repeating visual presentation of the first repeating pattern.

Without being bound by theory, by providing the first repeating pattern of apertures having a Longitudinal Orientation, the non-elastic region 221 appears coordinated with the Upper Gather Region 220 to enhance the directionality of the longitudinally continuous gathers of the Upper Gather Region 220, thus enhancing perception of high quality. The laminate having improved visibility and regularity of the first repeating pattern of apertures may be suitably provided by the methods below. Such method may also be advantageous in providing improved regularity of gathers which provide various functional benefits, and which are also aesthetically pleasing. The gathers of the present invention are continuous in the longitudinal direction, however, the direction of continuity may or may not completely match the longitudinal axis. The direction of gather is the direction in which the individual gathers are continuous, wherein the individual gathers are lined up with mountains and valleys repeating in the transverse direction.

Referring to FIG. 3A, the laminate may be made by bonding the elastic members 96 to at least one of the inner sheet 94 and the outer sheet 92, via a combination of an elastic bonding 230 and a vertical bonding 234. In FIG. 3A, the front elastic belt 84 is shown with the elastic members 96 and elastic bonding 230 expressed in solid lines. In FIG. 3A, the vertical bonding 234 is only expressed in the right side of the front elastic belt 84, and the side seams 32 are shown in an unjoined state.

What is meant by elastic bonding 230 herein is a bonding that bonds the elastic member 96 along the side edges 89 of the front and back elastic belts 84, 86. The elastic bonding 230 may be continuously applied to each elastic member 96 for a length of at least about 10 mm, or from about 10 mm to about 60 mm in the direction of stretch adjacent the side edges 89 of the front and back elastic belts 84, 86, including the length planned for side seaming. The elastic bonding 230 is to provide relatively strong bonding for the elastic member 96 and thus securely anchors the elastic member 96 within the laminate. The anchoring may be assisted by the side seaming. A certain percentage, or a greater percentage, of the dimension of the elastic bonding 230 along the side edges 89 may be seamed. The elastic bonding may also be utilized for an effective process of deactivating a limited transverse dimension of the elastic member 96. Referring to FIGS. 2 and 3A, the elastic member 96 may be deactivated in portions overlapping the absorbent core 62. In addition to the side edge regions, the elastic bonding 230T may be provided on both sides of the certain transverse dimension of the elastic member 96 which is planned to be deactivated, wherein the portion of the elastic member between the elastic bondings 230T are severed and deactivated. The deactivated portions of the elastic member is not shown in the Figures. Such deactivation may be referred to herein as tummy cut, and the deactivated region may match the non-elastic region 221.

What is meant by vertical bonding 234 herein is a bonding applied to at least one of the inner sheet 94 and the outer sheet 92 with intervals in the transverse direction for intermittently bonding the inner sheet 94 and the outer sheet 92. The vertical bonding 234 may also bond the elastic member 96 to at least one of the inner sheet 94 and the outer sheet 92. The vertical bonding 234 may only be provided to the outer sheet 92. Referring to FIG. 3A, vertical bonding 234 may be provided in a pattern for the entire area of the laminate. By providing vertical bonding 234 in a pattern for the entire area of the laminate, the vertical bonding 234 may serve as a bonding for the inner and outer sheets 92, 94 in regions where the elastic members 96 are severed. Vertical bonding 234 may be provided in regions adjacent the side edges 89 and thus overlapping regions where the elastic bondings 230 are provided. Alternatively, vertical bonding 234 may be provided only in regions where the elastic bondings 230 are not provided. Vertical bonding 234 may be provided at least in regions where the elastic member 96 is in active elasticity, wherein the elastic bondings 230 are devoid.

Figure 4A:
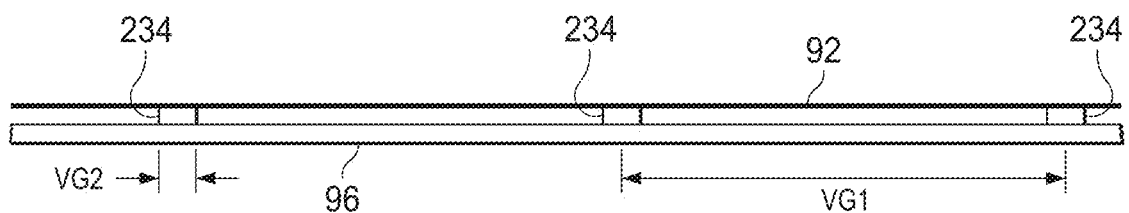
FIG. 4A is a schematic cross section view of FIG. 3B taken along section line 4-4 of FIG. 3B.
Figure 4B:
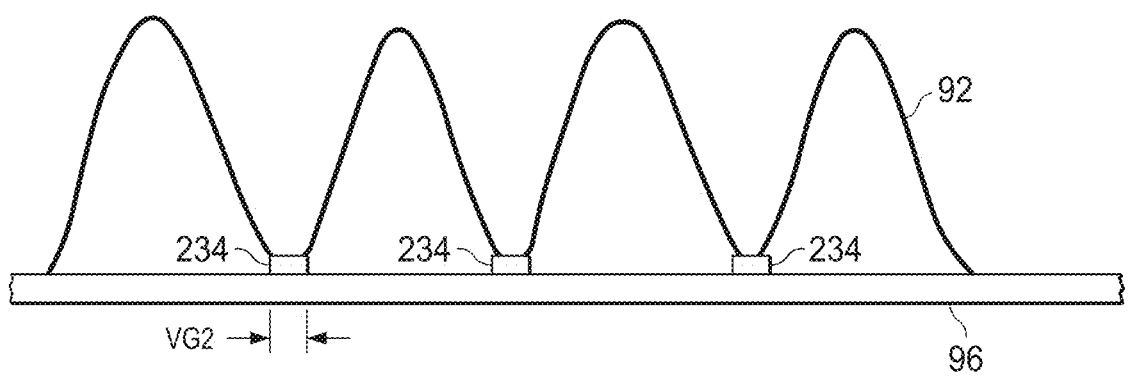
FIG. 4B is a schematic cross section view of 4A in a contracted state.

Referring to FIG. 4A, the vertical bonding 234 is observed in the thickness direction of the laminate along a single elastic member 96 in an extended state in the transverse direction, wherein FIG. 4A only expresses the outer sheet 92, vertical bonding 234, and the elastic member 96, wherein the vertical bonding 234 is provided on the outer sheet 92. The vertical bonding 234 may have a transverse dimension VG2 and provided as a continuous pattern aligned in the longitudinal direction, each longitudinal pattern of vertical bonding 234 spaced apart from each other with a transverse pitch VG1, wherein VG1 may be from about 2 mm to about 15 mm, and VG2 may be from about 0.2 mm to about 7 mm. When focusing on one elastic member 96, the vertical bonding 234 may provide intermittent bonding between the elastic member 96 and one of the inner sheet 94 and the outer sheet 92, or between the elastic member 96 and the outer sheet 92. This is in contrast with the elastic bonding 230 which is provided continuously along a certain length of the elastic member 96 in the direction of stretch. As such, in the region where the elastic member 96 is only intermittently bonded to one of the inner sheet 94 and the outer sheet 92, the portion of the elastic member 96 between the vertical bonding 234 in the transverse direction is unattached to any other part of the laminate. In FIG. 4A, the elastic member 96 is bonded to the outer sheet 92. Referring to FIG. 4B, when the elastic member 96 is allowed to contract, this causes the unattached portion of the outer sheet 92 to fold away from the elastic member 96 and form gathers. As such, compared to areas where the elastic bonding 230 is applied, the outer sheet 92 has less restriction in creating gathers.

Without being bound by theory, it is believed that by having less restriction for the inner sheet 94 and outer sheet 92 against the elastic members 96, this contributes in creating gathers of improved regularity, in that a significant amount of the inner and outer sheet materials 92, 94 existing between the vertical bondings 234 are available for creating gathers continuous in the longitudinal direction. Without being bound by theory, it is also believed that, by having less restriction for the inner and outer sheet materials 92, 94 against the elastic members 96, this allows improved stretchability of the elastic members 96, which may provide ease of application. Compared to elastic belts made only by elastic bonding 230 wherein all of the elastic members 96 are continuously bonded, the elastic belt 40 of the present invention may have a lower Stretch Circumference Force, according to the measurements herein. Further, despite such relatively low Stretch Circumference Force, the elastic belt 40 of the present invention may maintain a suitable Fit Circumference Force, according to the measurements herein. Without being bound by theory, it is also believed that, by having less restriction for the inner and outer sheet materials 92, 94 against the elastic members 96, this improves the breathability of the overall laminate, which may enhance skin health. Without being bound by theory, it is also believed that vertical bonding 234 provides a configuration wherein a greater percentage of the inner and outer sheet materials 92, 94 are available for forming the outer surfaces of the laminate when the elastic belt 40 is contracted, while the elastic members 96 remain positioned inside the thickness of the laminate. As such, the laminate is provided with improved loft and thickness, thus imparting improved comfort and softness when worn. Further, without being bound by theory, in that there is a great percentage of the inner and outer sheet materials 92, 94 available for forming the outer surfaces of the laminate in high regularity when the elastic belt 40 is contracted, this provides the body facing surface of the elastic belt 40 to have higher stiffness in the longitudinal direction, thus contributing in improved fit for preventing sagging. Still further, in that the elastic members are less visible when the elastic belt 40 is contracted, this further enhances the aesthetically pleasing regularity of gathers.

In order to make available for gathering a significant amount of the inner and outer sheet materials 92, 94 between the vertical bondings 234 in the transverse direction, VG1 may be from about 2 times to about 20 times, or from about 3.5 times to about 10 times of VG2.

By bonding, what may be utilized are any methods known in the art, such as use of hot melt adhesive, thermal energy, and ultrasonic energy. Bonding strength may be adjusted by the area of bonding, or by different adhesion or energy level provided by the bonding, for example, adjusting the amount and strength of an adhesive agent. The bonding strength of the elastic bonding 230 and the vertical bonding 234 may be the same or may be varied. The elastic bonding 230 and the vertical bonding 234 may be provided by the same hot melt adhesive.

Figure 3B:
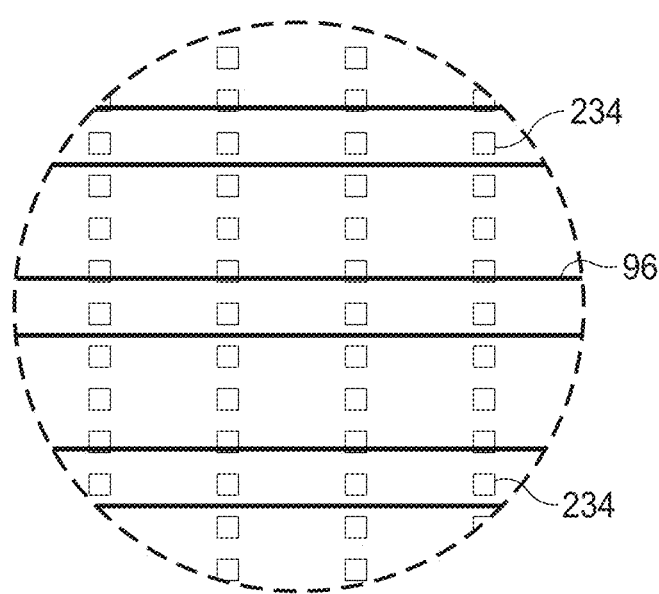
FIG. 3B is an expanded schematic plan view of FIG. 3A.

The vertical bonding 234 may be a continuous line extending in the longitudinal direction. Referring to FIG. 3B, the vertical bonding 234 may be discontinuous, or may be an array of discrete bondings aligned in the longitudinal direction. Each discrete vertical bonding 234 may have a longitudinal dimension of from about 0.5 mm to about 10 mm, and a longitudinal pitch of from about 1 mm to about 10 mm, or from about 0.8 mm to about 5 mm. By providing the vertical bonding 234 in an array of discrete bondings, the overall area of bonding may be decreased. This is advantageous for maintaining the laminate in a soft tactile sense, in that bonding may provide the inner and outer sheet material 92, 94 stiffer. Further, this may save material or energy for the bonding. Each discrete vertical bonding 234 may be provided in an appropriate longitudinal pitch such that there is at least one discrete bonding that bonds each elastic member 96, however, this is not essential. Rather, it is essential that there is at least one discrete vertical bonding 234 existing in each longitudinal spacing of the elastic members 96, such that the neighboring elastic members 96 do not contact each other. In that the elastic bonding 230 provides secure bonding of the elastic member 96 along the side seams, as well as the outer periphery of the non-elastic region 221, so long as there is at least one discrete vertical bonding 234 existing in each longitudinal spacing of elastic members 96, this prevents the elastic member 96 from moving away from its intended position. For an entire front elastic belt 84 or an entire back elastic belt 86 there may be no elastic member 96 bonded to the inner sheet 94 or the outer sheet 92 by a discrete vertical bonding 234. For an entire front elastic belt 84 or an entire back elastic belt 86, at least one to about 50% of the elastic members 96 may be bonded to the inner sheet 94 or the outer sheet 92 by the discrete vertical bonding 234. For an individual elastic member 96 along its activated length, some portions may be bonded by the discrete vertical bonding 234, while some portions may be left unbonded by the discrete vertical bonding 234.

Referring to FIG. 2, for the belt-type pant, the proximal edges 90 of the front and back belt 84, 86 may be provided with an end seal in order to keep the inner and outer sheets 92, 94 closed at the proximal edges 90 and thus prevent elastic members 96 from being accessible. Such unaccessibility of elastic members 96 may be particularly advantageous when the article is for a young wearer. Alternatively or additionally, the elastic member 96 which is positioned closest to the proximal edge 90 may be provided with a bonding along the transverse dimension of the elastic member 96 in state of active elasticity.

Referring to FIG. 2, the elastic member 96 may be made by a plurality of elastic strands 96 running parallel to each other in the transverse direction, wherein the laminate has at least a region wherein the elastic strands 96 have a longitudinal pitch of from about 2 mm to about 20 mm, or from about 3 mm to about 12 mm, or from about 3 mm to about 7 mm. At least some of the Upper Gather Region 220 may have the elastic strands 96 disposed in a longitudinal pitch of from about 3 mm to about 7 mm. Without being bound by theory, it is believed that such longitudinal pitch of the elastic strands 96, combined with the transverse pitch of the vertical bonding 234 as described above, contributes in creating gathers of improved regularity by providing the appropriate longitudinal continuity of material provided by the stiffness of the inner and outer sheet materials 92, 94. At least a portion of the Upper Gather Region 220 may have the elastic strands 96 disposed in a constant longitudinal pitch, the constant pitch being from about 2 mm to about 20 mm, or from about 3 mm to about 12 mm, or from about 3 mm to about 7 mm, with a deviation of no more than about 1.5 mm. Without being bound by theory, it is believed that such constant pitch of the elastic strands 96 contributes in creating gathers of improved regularity and continuity.

The front and back elastic belts 84, 86 may be made by running the continuous inner and outer sheet materials as well as the continuous elastic strands along the transverse axis of the article, and bonding them via the elastic bondings 230 and vertical bondings 234. During manufacture, the continuous inner and outer sheet materials and continuous elastic strands may be transferred in the machine direction, wherein the machine direction of manufacture matches the transverse axis TX of the article. In such manufacturing process, the vertical bondings 234 are provided continuous or discretely aligned in the cross machine direction and intermittently spaced apart by a pitch of VG1 in the machine direction of manufacture. The longitudinal pattern of vertical bondings 234 may match the cross machine direction of manufacture, namely the longitudinal axis LX of the article, or may be slightly titled for better control of the process, particularly when the vertical bonding 234 is provided by applying bonding on a rotating roller. The vertical bonding 234 may be tilted with an angle from the cross machine direction of manufacture, namely the longitudinal axis LX of the article, by from about 0.1 to about 30 degrees in either clock-wise or counterclock-wise direction, or from about 0.1 to about 15 degrees in either clock-wise or counterclock-wise direction.

Figure 5A:
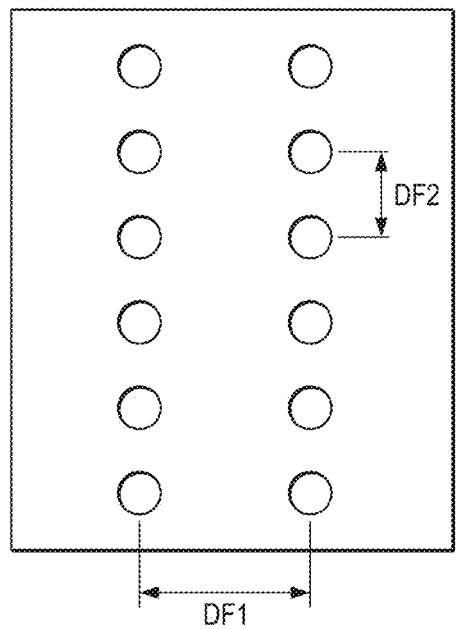
FIG. 5A is a schematic plan view of the elastic belt of the present invention.

Referring to FIG. 5A, at least the outer sheet 94 comprises a first repeating pattern of apertures wherein the apertures are aligned in the longitudinal direction. The apertures of the first repeating pattern may be spaced apart from each other with a transverse pitch of DF1, wherein VG1 is greater than DF1, or wherein VG1 is at least 1.5 times, or at least 2 times, of DF1. Without being bound by theory, such first repeating pattern of apertures provided in relationship with the vertical bonding assists the nonwoven material for making the outer sheet 94 to be folded within dimension VG1, the folding being continuous in the longitudinal direction. As such, the regularity of apertures are enhanced, as well as the continuity of the gathers are enhanced. The first repeating pattern may or may not be registered with the longitudinal pattern of the vertical bonding 234. In fact, it is the finding of the present invention that, even when the first repeating pattern is not registered with the longitudinal pattern of the vertical bonding 234, this still enhances the regularity of gathering as well as the visibility of the apertures. In that registration of the first repeating pattern and the longitudinal pattern of the vertical bonding 234 may require precision of process, such registration may be omitted. Even when the first repeating pattern is not registered with the longitudinal pattern of the vertical bonding 234, by providing DF1 and VG1 in a relationship other than multiple number of integers, certain percentage of the apertures of the first repeating patterns fit within the longitudinal patterns of the vertical bonding 234 and thus made visible.

Figure 7A:
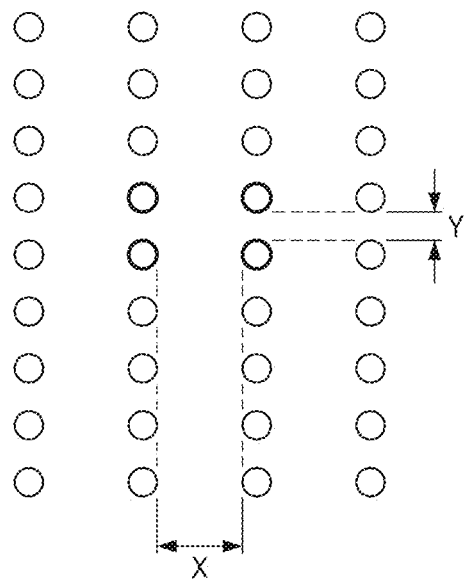
FIGS. 7A-7D are related to the Longitudinal Orientation measurement herein.
Figure 7B:
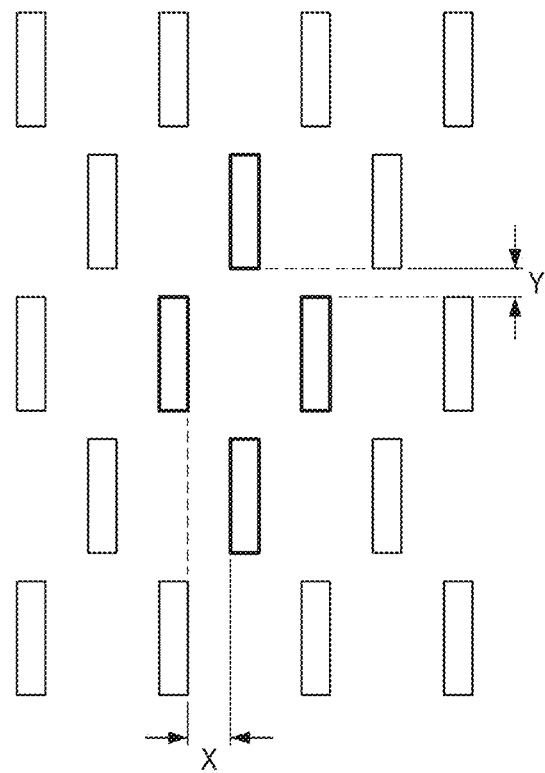
Figure 7C:
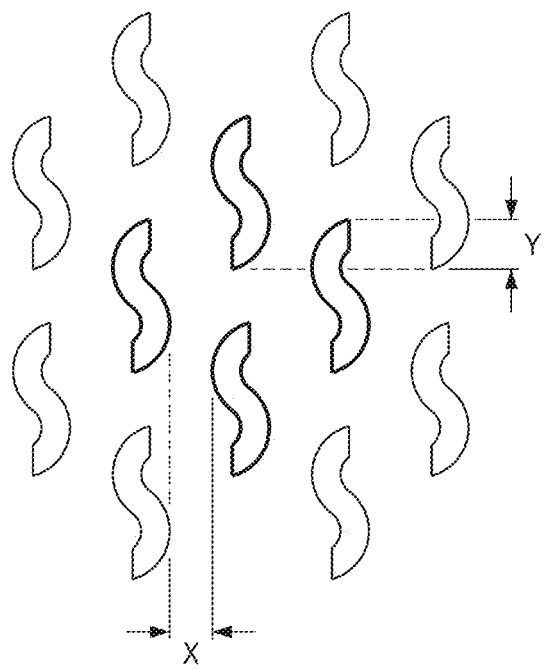
Figure 7D:
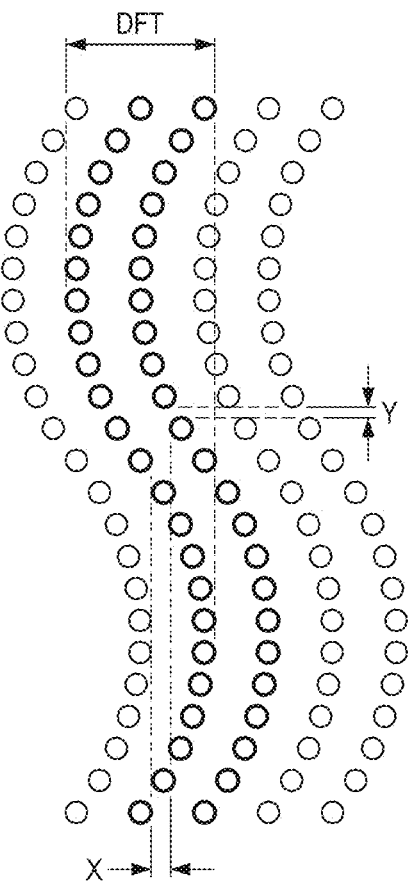

Referring to FIGS. 7A-7D, the first repeating pattern of apertures may have a longitudinal repeating unit. Namely, when hypothetically connecting the apertures of closest adjacency in the longitudinal direction, there is provided a longitudinally continuing line. This longitudinally continuing line is referred to as the longitudinal repeating unit. The longitudinal repeating unit may be a straight line or a sinusoidal curve. Referring to FIG. 7D, when the longitudinal repeating unit is a sinusoidal curve, the curve may have a repeating unit having a transverse dimension DFT within that of VG1. By providing the first repeating pattern in such configuration, the continuity of the gathers are enhanced. The transverse dimension DFT of the longitudinal repeating unit may be less than VG1 and may be less than DF1.

Referring to FIG. 5A, the apertures within the first repeating pattern of apertures are further spaced apart from each other with a longitudinal pitch of DF2, wherein DF2 is not more than about 5 mm, and DF2 is not greater than DF1. By providing the apertures in such arrangement, this facilitates the gather folding in the longitudinal direction as described above. When the first repeating pattern has a longitudinal repeating unit in a straight line, the longitudinal repeating unit may be tilted in the same degree as the vertical bonding 234, as described above. Namely, the longitudinal repeating unit may be tilted from about 0.1 to about 30 degrees, or from about 0.1 to about 15 degrees in either clock-wise or counterclock-wise direction from the longitudinal axis of the article. This is believed to enhance the folding of the inner and outer sheet material 92, 94 in the direction of the gather continuity. The laminate may comprise a portion wherein the elastic strand spacing comprises at least 2 apertures. By providing a plurality of apertures between the elastic strand spacing in the longitudinal direction, this is also believed to enhance the folding of the inner and outer sheet material 92, 94 in the direction of the gather continuity.

Figure 5B:
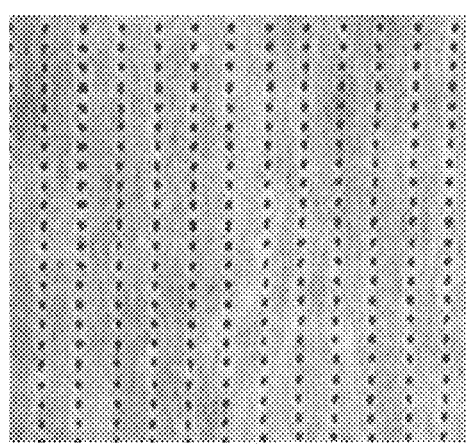
FIG. 5B is a plan view of the elastic belt of the present invention in a stretched state.
Figure 5C:
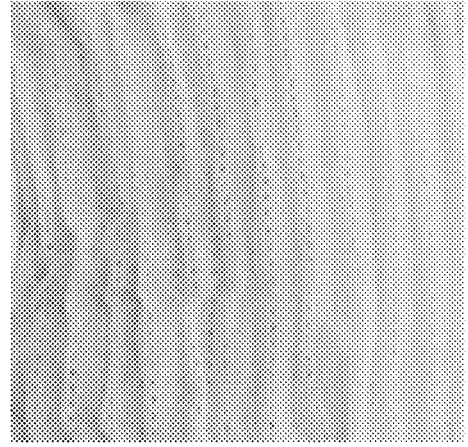
FIG. 5C is a plan view of the elastic belt of FIG. 5B in a contracted state.

The individual aperture may be in the shape of a circle, oval, or polyhedron, while having an aspect ratio of no more than about 2. The individual aperture may have a minor radius of at least about 0.1 mm, or from about 0.1 mm to about 0.8 mm. What is meant by minor radius herein is the radius of a circle, minor radius of an oval, or one half the shortest dimension of a polyhedron. Apertures of such size and shape may be visible to the naked eye on the garment-facing surface, and thus connote breathability and high quality of the gather, as well as the entire laminate. Further, by providing VG1 greater than DF1, the apertures are positioned on the folding as described above, thus the visibility of the apertures are enhanced even when the gathers are in contracted state. FIG. 5B is a plan view of the elastic belt of the present invention in a stretched state, whereas FIG. 5C is the same elastic belt in a contracted state. In the elastic belt of FIGS. 5B-5C, the VG1 is about 1.5 times that of DF1. As can be seen in FIG. 5C, by providing the VG1 and DF1 relationship as such, at least one longitudinal row of apertures are continuously folded in the longitudinal manner to provide a longitudinal continuous gather, while the apertures are situated nearby the mountain of each gather. As such, breathability as well as breathability perception are enhanced. Further, by providing DF1 somewhat greater than DF2 and the individual aperture in an aspect ratio of no more than about 2, the first repeating pattern takes a Longitudinal Orientation of apertures, as described in further detail below. By providing the first repeating pattern of apertures in Longitudinal Orientation in the non-elastic region 221, the non-elastic region 221 appears coordinated with the Upper Gather Region 220 to enhance the longitudinally continuing gathers of the Upper Gather Region 220.

The inner sheet 94 for making the front and back elastic belts may comprise a second repeating pattern of apertures. This may further enhance the breathability of the elastic belt 40. The second repeating pattern of apertures on the inner sheet 94 may be the same as the first repeating pattern of apertures on the outer sheet 92 and matched to provide breathability. The second repeating pattern of apertures on the inner sheet 94 may be different from the first repeating pattern of apertures on the outer sheet 92 in one or more of size, longitudinal pitch, or transverse pitch. Such difference in first and second repeating patterns may prevent the skin of the wearer from being visible from the garment-facing side through the apertures.

The tensile stress (N/m) of the entirety of the front and back elastic belts 84, 86, respectively, may be profiled in order to provide the functional benefits of the present invention, such as ease of stretch and application, while also maintaining certain force during wear, to prevent the article from sagging after loading. When the elasticity of the front and back elastic belts 84, 86 are provided by a plurality of elastic members 96 running in the transverse direction, the tensile stress may be adjusted by one or more of the following methods; 1) elongation rate of the elastic member 96; 2) density (dtex) of the elastic member 96; 3) longitudinal interval of multiple elastic members 96; and 4) effective length of elasticity of the elastic member 96 in the transverse direction. By elongation, "0% elongation" is meant the original length of the elastic member. When a portion of an elastic member 96 is removed of its elasticity, the remainder of the intact elastic member capable of imparting elasticity is defined as the "effective length of elasticity of an elastic member".

Referring to FIG. 2, the front and back elastic belts 26, 28 may each be divided into 4 zones spanning in the transverse direction and defined of its position from the distal edge 88 to the proximal edge 90 relative to the percentage of the seam length LS. In the example of FIG. 2, the entirety of the length of the belt side edge 89 of the front region 26 is the front belt 84, and is seamed with a certain length of the belt side edge 89 of the back region 28 which is the back belt 86 to define a seam length LS. When seam length LS is considered 0% at the distal edge 88 and 100% at the proximal edge 90 of the side seam 32, the zones are defined as such: 0-25% is the waist zone 102, 25-50% is the distal tummy zone 104, 50-85% is the proximal tummy zone 106, and 85-100% is the leg zone 108. When there is an elastic member disposed at 25% from the distal edge 88, such elastic member is considered to be included in the waist zone 102. When there is an elastic member disposed at 50% from the distal edge 88, or 85% from the distal edge 88, such elastic member is considered to be included in the proximal tummy zone 106.

In the article of the present invention, the tensile stress of the front proximal tummy zone 106 may be provided higher than the tensile stress of any of the front waist zone 102, the front distal tummy zone 104, or the front leg zone 108. The tensile stress of the front proximal tummy zone 106 may be higher than the tensile stress of any other zone, either in the front or the back. The tensile stress of the back distal tummy zone 104 may be provided higher than any of the tensile stress of the back waist zone 102, the back proximal tummy zone 106, or the back leg zone 108. When comparing the 4 zones each of the front belt and the back belt, the tensile stress may be provided greatest in the order of: the front proximal tummy zone 106, followed by the back distal tummy zone 104. Without being bound by theory, such profiling of the tensile stress per zone is believed to provide the article of the present invention with a shaped elastic belt 40 that conforms well to a human body, particularly to a lower torso of a child of less than 36 months of age, and therefore provide good fit and comfort to the wearer, without compromise of sagging prevention or leakage prevention. Namely, the front proximal tummy zone 106 is subject to high tensile stress such that the article may be anchored against the wearer's trochanter, while leaving more area for the back proximal tummy zone 106 to accommodate the wearer's buttock. As long as the article is anchored securely at the trochanter, the Upper Gather Region 220 may be provided in relatively lower tensile stress. Without being bound by theory, it is believed that such relatively lower tensile stress contributes in providing the Upper Gather Region 220 with improved regularity of gathering, as well as soft fit.

For the belt-type pant, the longitudinal length LB of the back elastic belt 86 and the longitudinal length LF of the front elastic belt 84 may be provided the same, or the back elastic belt 86 may have a greater longitudinal length LB as in FIG. 2. Referring to FIGS. 1B and 2, when the wearable article is assembled to form the waist opening and the leg openings, the wearable article 20 is folded along the transverse centerline TX such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line TX such that the proximal portion of the back side panel 82 extends toward the crotch panel 56 of the main body 38 beyond the front proximal edge 90. The side edge of the proximal portion of the back side panel 82 may not be joined to anywhere and free from attachment. Thus, the proximal portion of the back side panel 82 provides a buttock cover 95, as in FIG. 1B.

The outer sheet 92 of the present invention may be a nonwoven having a basis weight of from about 10 gsm to about 55 gsm, or from about 10 gsm to about 35 gsm, and may have a fiber diameter of from about 0.8 dpf to about 6 dpf. The fiber diameter is described in denier per filament (dpf) used in the industry, which is grams/9,000 meters of length of fiber. The outer sheet 92 nonwoven may be made by processes such as spunbond, spunlace, carded or air-laid; and may comprise fibers and/or filaments made of polypropylene (PP), polyethylene (PE), polyethylene phthalate (PET), polylactic acid/polylactide (PLA) or conjugate fibers (such as PE/PET, PE/PP, PE/PLA) as well as natural fibers such as cotton or regenerated cellulosic fibers such as viscose or lyocell. The outer sheet 92 nonwoven may be a multilayer or composite structure combining nonwovens made by different processes and fibers such as combining spunbond and carded nonwovens. The outer sheet 92 nonwoven may be made by biodegradable material, or derived from renewable resources. Exemplary material for the outer sheet 92 include: air-through carded nonwoven having a thickness of at least about 50 μm, or at least about 80 μm, or at least about 200 μm. Such material may provide a soft lofty feeling to the garment-facing side. Suitable for the outer sheet 92 nonwoven of the present invention are air-through carded nonwoven material made of co-centric bicomponent fiber, crimping fiber made through core eccentric bicomponent filament or side by side bicomponent filament. Non-limiting examples of materials suitable for the outer sheet 92 nonwoven of the present invention include: 12-45 gsm air-through carded nonwoven substrate comprising PE/PET bi-component fibers, such as those available from Beijing Dayuan Nonwoven Fabric Co. Ltd. or Xiamen Yanjan New Material Co. Ltd., and 8-45 gsm spun melt nonwoven substrate comprising PP monofilament or PE/PP bi-component fibers, such as those available from Fibertex or Fitesa.

The inner sheet 94 of the present invention may be a nonwoven having a basis weight of from about 5 gsm to about 45 gsm, or from about 5 gsm to about 35 gsm. The inner sheet 94 nonwoven may have a fiber diameter of from about 0.5 dpf to about 4 dpf. The inner sheet 94 nonwoven may be made by processes such as spunbond, spunlace, carded or air-laid; and may comprise fibers and/or filaments made of polypropylene (PP), polyethylene (PE), polyethylene phthalate (PET), polylactic acid/polylactide (PLA) or conjugate fibers (such as PE/PET, PE/PP, PE/PLA) as well as natural fibers such as cotton or regenerated cellulosic fibers such as viscose or lyocell. The inner sheet 94 nonwoven may also be a multilayer or composite structure combining nonwovens made by different processes and fibers such as combining spunbond and carded nonwovens. The inner sheet 94 nonwoven may be made by biodegradable material, or derived from renewable resources. Non-limiting examples of materials suitable for the inner sheet 94 nonwoven of the present invention include: 12-30 gsm air-through carded nonwoven substrate made of PE/PET bi-component staple fiber, such as those available from Beijing Dayuan Nonwoven Fabric Co. Ltd. or Xiamen Yanjan New Material Co. Ltd., and 8-30 gsm spun melt nonwoven substrate comprising PP monofilament or PE/PP bi-component fibers, such as those available from Fibertex or Fitesa.

The basis weight of the outer sheet 92 and the inner sheet 94 may be adjusted such that the basis weight of the inner sheet 94 is not greater than the basis weight of the outer sheet 92. Thus, the outer sheet 92 may be provided with a soft lofty tactile sense which connotes high quality, while the inner sheet 94 may be kept thinner and conforming to the outer sheet 92, thus saving cost. Further, without being bound by theory, by providing the basis weight relationship as such, it is believed that skin sweating is effectively transported to the outer sheet 92 and outside the laminate, while preventing the transported sweat back to the inner sheet 94. The hydrophilicity/hydrophobicity of the outer sheet 92 and the inner sheet 94 may be adjusted such that the hydrophilicity of the outer sheet 92 is higher than that of the inner sheet 94. Without being bound by theory, it is believed that such gradient of hydrophilicity is advantageous in transporting skin sweat from the inner sheet 94 to the outer sheet 92 and outside the laminate. The inner sheet 94 nonwoven may be inherently hydrophobic. The inner sheet 94 nonwoven may be provided hydrophobicity by treating with hydrophobic melt additives into polymer resin in the fiber making process, or by applying hydrophobic additives after the nonwoven is formed. The outer sheet 92 nonwoven may inherently be hydrophobic, and thus provided relatively more hydrophilic than the inner sheet 94 by treating with hydrophilic melt additives into polymer resin in the fiber making process, or by applying hydrophilic additive after the nonwoven is formed.

As described above, the outer sheet 92 may be provided with apertures. Apertures may be made by female-male hot pin process, hole punching process, hydroentanglement process using water jets and a screen to create holes, and combinations thereof. The apertures may be made by creating a plurality of weakened locations by heat, pressure, or ultrasonic energy, followed by incrementally stretching, causing said nonwoven web to rupture at the weakened locations such as described in U.S. Pat. No. 5,628,097. Such rupturing method may be particularly useful for nonwovens using spunbonded fibers and meltblown fibers. The apertures may be three-dimensional, nonhomogenous, unaligned and forming a pattern as described in PCT Publication WO 2016/73712. The inner sheet 94 may also be provided with apertures for breathability. Apertures for the inner sheet 94 may be made in the same or different process, size, and density as the outer sheet 92. Providing apertures may alter the stiffness of the inner or outer sheet 92, 94. The stiffness of the outer sheet 92 in the longitudinal direction and the transverse direction may be adjusted to provide the desired longitudinally continuing gathers.

The garment-facing side of the crotch region 30 of the present article may be provided with a third repeating pattern of apertures. The third repeating pattern of apertures may also have a Longitudinal Orientation, according to the measurements herein. The third repeating pattern of apertures may have a common element as that of the first repeating pattern of apertures. By coordinating the visible apertures in the crotch region 30 and the front and/or back elastic belt 84, 86, the integral undergarment like appearance of the article may be enhanced. Further, for the belt-type pant, coordination of the visible apertures in the crotch region 30 and the front and/or back elastic belt 84, 86 may help alleviate the visibility of the border between the different parts.

Whole Article Force Measurement

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity.

Figure 6:
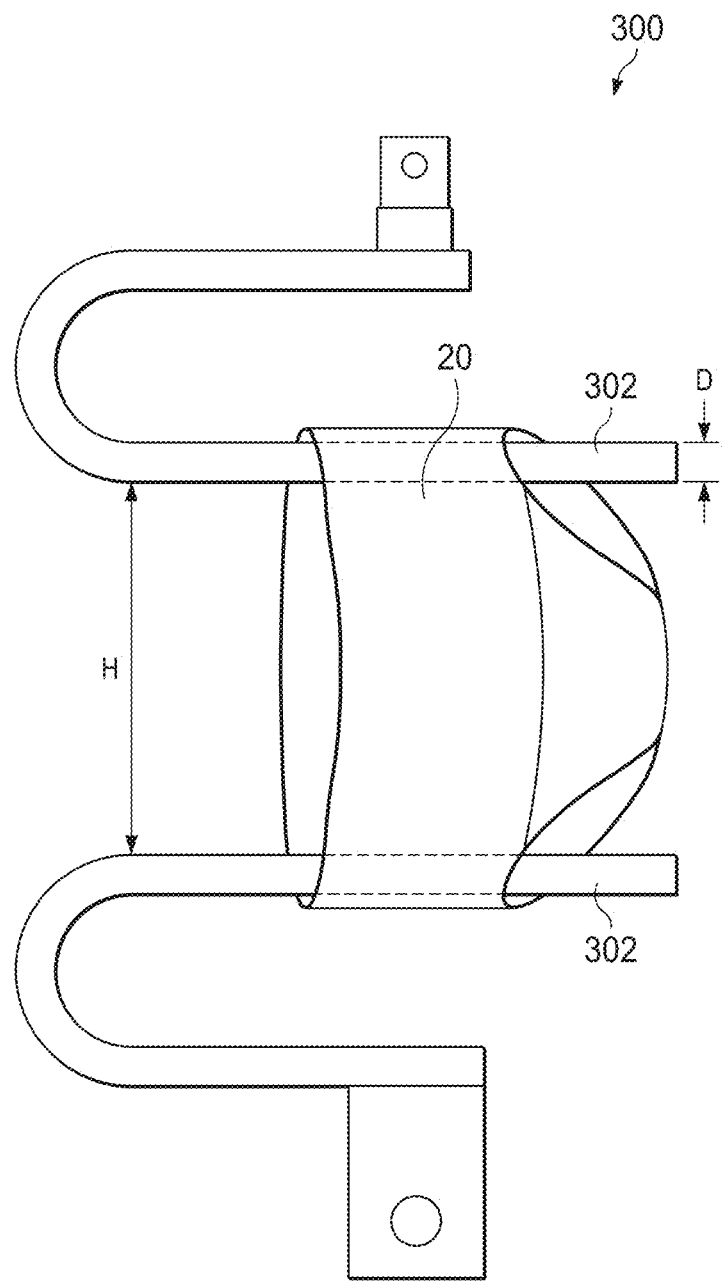
FIG. 6 is a schematic view of an example of a hanger-type sample holding fixture according to the "Whole Article Force Measurement".

The tensile tester is fitted with hanger-type sample holding fixtures 300 as shown in FIG. 6. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

Gauge Circumference=$2 \times (H+D+\pi D/2)$ where H is the vertical gap between the horizontal bar sections 302, and D is the outer diameter of the bar.

The instrument is set up to go through the following steps:

| | |
|---|---|
| Crosshead Speed | 254.0 mm/min |
| Final Load Point | 19.61N |
| Hold Time | 0 |
| Number of Cycles | 1 |
| Data Acquisition Rate | 50 Hz |

An article 20 sample is inserted onto the upper horizontal bar section 302 so that the bar passes through the waist opening and one leg opening of the article. The crosshead is raised until the specimen hangs above the lower bar and does not touch lower bar 302. The load cell is tared and the crosshead is lowered to enable the lower bar 302 to be inserted through the waist opening and other leg opening without stretching the article. The article is adjusted so that the longitudinal centerline LX of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1N, while taking care not to add any unnecessary force. The gauge circumference at this point is the Initial Gauge Circumference. The test is initiated and the crosshead moves up at 254 mm/min until a force of 19.6N is attained, then the crosshead immediately returns to the Initial Gauge Circumference at the same speed. The maximum circumference at 19.6N and the force at 70% of the maximum circumference during the loading segment and unloading segment of the test are recorded.

The maximum circumference (mm) at 19.6N is defined as the Full Stretch Circumference W1. The Full Stretch Circumference (mm)×0.7 is defined as the 70% Stretch Circumference W2. The force (N) during the loading segment of the test at 70% Stretch Circumference is defined as the Stretch Circumference Force. The force (N) during the unloading segment of the test at 70% Stretch Circumference is defined as the Fit Circumference Force. Five samples are analyzed and their average are calculated and reported to the nearest 1 mm or 0.01N, respectively.

Longitudinal Orientation

This measurement is provided for a visible pattern of apertures, which is defined as a visually recognizable pattern by the naked eye when observed from a distance of 10 cm. Referring to FIGS. 7A-7D, identify a Basic Unit which is a minimum complete unit of the pattern that repeats to create the pattern and is capable of surrounding a specific area. Within the Basic Unit, the closest adjacent apertures in the longitudinal direction and the transverse direction are identified. The spacing between the closest adjacent apertures in the longitudinal direction Y and the same in the transverse direction X are measured by a scale (unit: 0.1 mm). The Y spacing and/or X spacing may be negative, as is the case for the Y spacing in FIG. 7C.

Those patterns having the X spacing longer than the Y spacing by at least 10% are considered having a Longitudinal Orientation. Five portions of the same pattern are analyzed and their average are calculated and reported to the nearest %.

EXAMPLES

Examples 1, A, B, and D are obtained as such, and subject to tests as described below.

Example 1 has the configuration, elastic profile, and other properties as in FIG. 2 and Table 1 below made by experimental machinery with Lot Not. EXP-19-DZ7410. The first repeating pattern of apertures provided on the outer sheet were in Longitudinal Orientation.

TABLE 1

| | Dtex/elongation %/number of elastic members |
|---|---|
| Front waist zone | 470 Dtex/160%/4 with elastic pitch of 6 mm |
| Front distal tummy zone | 470 Dtex/160%/2 |
| | 470 Dtex/230%/2 with tummy cut (*1) |
| Front proximal tummy zone | 940 Dtex/230%/8 with tummy cut (*1) |
| Front leg zone | 470 Dtex/130%/2 with tummy cut (*1) |
| Back waist zone | 470 Dtex/160%/4 with elastic pitch of 6 mm |
| Back distal tummy zone | 940 Dtex/160%/4 with elastic pitch of 6 mm |
| Back proximal tummy zone | 470 Dtex/230%/4 |
| | 470 Dtex/270%/4 with elastic pitch of 12 mm and tummy cut (*1) |
| Back leg zone | 470 Dtex/270%/2 with tummy cut (*1) |
| Outer sheet material | Air-through carded nonwoven made by Beijing Dayuan having basis weight of 20 gsm |
| Outer sheet aperture minor radius | 0.45-0.55 mm |
| Outer sheet DF1 | 3.8 mm |
| Outer sheet DF2 | 2 mm |
| VG1 | 7 mm |
| VG2 | 1 mm |

(*1) "Tummy cut" in Table 1 refers to deactivation of elasticity at the transverse central area of elastic strands resulting in 68% effective length of elasticity.

Example A: Size 4 (L-size) uni-body type pant article sold by the tradename of "Merries" having Lot No. 20190422, purchased in the China market.

Example B: Size 4 (L-size) uni-body type pant article sold by the tradename of "GooN Super Premium—Feather" having Lot No. 20181004, purchased in the China market.

Example D: Size 4 (L-size) belt-type pant article sold by the tradename of "Teddy Bear More than thinner" having Lot No. 20190424D, purchased in the China market.

Show and Feel Test 30 panelists who were caregivers of babies using Size 4 (L size) pant diapers and having a mixture of usage experience of major brands of similar price range used in the test were recruited. There were about equal number of caregivers of boy and girl babies in the age group of 25-36 years old. 15 finished product test samples were shown worn on a mannequin, and further provided to the panelist to touch and feel with their hands. All of the test sample were provided without any artwork. For Examples A, B, and D which were purchased from the market, the artwork was removed by removing the printed backsheet, and then reconstructing the sample replacing the backsheet with one that has no printing to make a finished product. Care was taken not to deteriorate the gather quality when reconstructing the sample. Each respondent was asked to fill in a questionnaire individually after observing and touching the test sample one by one. In the questionnaire, there were 7 values as found in Table 4, and each respondent was requested to rate the test samples against those values using the 5 ratings, which were scored as such: "Poor"=0, "Fair"=25, "Good"=50, "Very Good"=75, and "Excellent"=100. The scores were averaged and the scores were averaged.

Among 15 test samples tested, information for Examples 1, A, B, and D are extracted below in Table 2. Not all of the respondents rated all of the products, thus "Base Size" indicates the number of respondents.

TABLE 2

| Value | Example 1 | Example A | Example B | Example D |
|---|---|---|---|---|
| Base Size | 20 | 29 | 28 | 29 |
| Overall | 68 ABD (*3) | 35 | 46 | 47 A |

TABLE 2-continued

| Value | Example 1 | Example A | Example B | Example D |
|---|---|---|---|---|
| Distinctiveness | 53 AD | 23 | 41 A | 32 |
| High Quality | 64 AD | 34 | 54 A | 41 |
| Craftsmanship | 65 AD | 34 | 53 A | 41 |
| Breathability | 69 AD | 22 | 45 A | 49 A |
| Soft | 63 A | 40 | 59 A | 59 A |
| Comfort | 66 ABD | 38 | 53 A | 52 A |

(*3) The markings of Example numbers after the scores indicate "statistically significantly better" against the marked Example at 90% confidence level. For example, "Overall" rating of Example 1 was statistically significantly better than each of Examples A, B, and D.

According to this test, Example 1 which meets the requirements of the present invention have statistically significantly higher overall acceptance than Examples A, B, and D, and is also statistically significantly better or superior in all of the other values.

The article of Example 1 provides aesthetically pleasing regularity of gathers and good visibility of apertures in the Upper Gather Region 220. The article of Example 1 also provides improved stretchability for ease of application, improved fit for preventing sagging, improved comfort and softness, and improved breathability for skin health.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article continuous in a longitudinal direction and a transverse direction comprising a front elastic belt region, a back elastic belt region, a crotch region, a waist opening, and a pair of leg openings; the crotch region extending longitudinally between the front elastic belt region and the back elastic belt region; the front and back elastic belt regions each comprising a laminate, the laminate comprising an inner sheet, an outer sheet, an elastic member running in the transverse direction, an elastic bonding which continuously bonds the elastic member for at least about 10 mm in the direction of stretch in a region adjacent side edges of the front and back elastic belt regions, and a vertical bonding applied to at least one of the inner sheet and the outer sheet with intervals in the transverse direction to intermittently bond the inner sheet and the outer sheet, the vertical bonding having a transverse dimension VG2 and spaced apart from each other with a transverse pitch VG1;

wherein the elastic member is a plurality of elastic strands running parallel to each other in the transverse direction with a longitudinal pitch of from about 2 mm to about 20 mm;

wherein at least the outer sheet comprises a first repeating pattern of apertures wherein each aperture has an aspect ratio of no more than about 2 and a minor radius of at least about 0.1 mm, the first repeating pattern of apertures spaced apart from each other with a longitudinal pitch DF2 of no more than about 5 mm, and spaced apart from each other with a transverse pitch DF1, wherein VG1 is greater than DF1, and wherein the first repeating pattern of apertures have a Longitudinal Orientation, according to the measurements herein; and wherein the first repeating pattern of apertures comprise a longitudinal repeating unit, wherein a transverse dimension DFT of the longitudinal repeating unit is less than VG1; and wherein VG1 is from 9 mm to about 15 mm; and wherein the vertical bonding is discontinuous and aligned in the longitudinal direction, and wherein the vertical bonding is an array of discrete bondings aligned in the longitudinal direction wherein each discrete bonding has a longitudinal dimension of from about 0.5 mm to about 10 mm and a longitudinal pitch of from about 0.8 mm to about 5 mm, wherein there is at least one discrete bonding between each elastic strand.

2. The article of claim 1, wherein the laminate comprises a region wherein the elastic strands have a longitudinal pitch of from about 3 mm to about 7 mm.

3. The article of claim 2, wherein the laminate comprises a portion wherein an elastic strand spacing comprises at least 2 apertures.

4. The article of claim 1, wherein VG2 is from about 0.2 mm to about 7 mm.

5. The article of claim 1, wherein the inner sheet comprises a second repeating pattern of apertures, wherein the second repeating pattern of apertures is different from the first repeating pattern of apertures in one or more of size, longitudinal pitch, or transverse pitch.

6. The article of claim 1, wherein the crotch region comprises a third repeating pattern of apertures, wherein the third repeating pattern of apertures having a Longitudinal Orientation, according to the measurements herein.

\* \* \* \* \*